United States Patent [19]

Smith et al.

[11] Patent Number: 4,594,549
[45] Date of Patent: Jun. 10, 1986

[54] UNIFORM FIELD GENERATING EDDY CURRENT TESTING PROCESSING METHOD AND APPARATUS

[75] Inventors: Eugene Smith, Palm Beach Gardens; Thomas Posluszny, Juno Isles, both of Fla.

[73] Assignee: United Technologies Corporation, Hartford, Conn.

[21] Appl. No.: 609,906

[22] Filed: May 11, 1984

[51] Int. Cl.$^4$ .................... G01N 27/90; G01R 33/12
[52] U.S. Cl. .................................. 324/232; 324/233; 324/242
[58] Field of Search ............... 324/228, 232, 233, 235, 324/239–243, 247

[56] References Cited

U.S. PATENT DOCUMENTS

| | | | |
|---|---|---|---|
| 2,694,793 | 11/1954 | Martin | 324/247 |
| 3,526,886 | 9/1970 | Lubich | 324/243 |
| 3,535,625 | 10/1970 | Pratt | 324/233 |
| 4,063,230 | 12/1977 | Purinton et al. | 324/233 X |

FOREIGN PATENT DOCUMENTS

| | | | |
|---|---|---|---|
| 42792 | 4/1977 | Japan | 324/242 |
| 631987 | 11/1949 | United Kingdom | 324/232 |

Primary Examiner—Gerard R. Strecker

[57] ABSTRACT

A uniform eddy current is produced in a part and the field is probed in several orthogonal positions by two coils to yield, for each position and for each coil, a signal that manifests the phase difference between the field and the signal producing the current and a signal that manifests the relative strength of the field.

3 Claims, 2 Drawing Figures

UNIFORM FIELD GENERATING EDDY CURRENT TESTING PROCESSING METHOD AND APPARATUS

CROSS REFERENCE TO RELATED APPLICATIONS

These applications are assigned to the assignee of this application and disclose and claim related subject matter: UNIFORM INTERROGATING FIELD DRIVER by Eugene Smith, Ser. No. 579,226, filed on Feb. 10, 1984; UNIFORM EDDY CURRENT FIELD MEASUREMENT SYSTEM, also by Eugene Smith, Ser. No. 579,225, filed on Feb. 10, 1984; ROTATING PROBE FOR AUTOMATED ORIENTATION, by Thomas Posluszny, Paul Schlie and Kévin Smith, Ser. No. 580,505, filed on Feb. 15, 1984; and EDDY CURRENT TESTING, by Eugene Smith, Ser. No. 609,907, filed on May 11, 1984.

DESCRIPTION

1. Technical Field

Electrically conductive parts can be inspected for defects by generating eddy currents in the part and detecting the altered electromagnetic energy created by a surface or near surface defect, and this invention relates to methods and apparatus for performing that process.

2. Background Art

In eddy current testing an electromagnetic field is employed to produce an alternating eddy current in the part, which, because of the skin effect, flows generally along the surface of the part, following its contour. This current may also be induced in the part by means of contact electrodes through which the current directly flows through the part, this being one type of eddy current test technique known as contact testing. As a result of this eddy current flow in the surface of the part, there is a complex radiated electromagnetic pattern which represents the surface or near surface characteristics. A defect or property variation (e.g., structure) in the part causes a change in this radiated field, which can be detected, in a gross sense, to identify the presence of the defect, its location, but not its geometry.

Contemporary eddy current testing does not provide a three-dimensional definition of the surface or near surface characteristics. Available approaches are only concerned with identifying a defect. Usually this is done with an electromagnetic pickup that is located so that it produces a signal from the field EM (electromagnetic) produced by the current that flows in the conductive surface area or by measuring the voltage created by the eddy current. Known as contact testing, this technique is not satisfactory for some articles.

Roughly the same approach is used in testing nonconductive, but magnetic parts, although the criteria are different for fundamental reasons. A magnetic field, not a current, is impressed in the part, from a permanent magnet or an electromagnet, for example. The magnetic field is constrained in the magnetic part due to its reluctance, except, that is, at flaws or cracks. One magnetic test uses two pairs of coils, one of which is further than the other from the surface of the part, and these coils are arranged for differentially summing their outputs. This is done to sense the difference in magnetic field at the two distances from the surface of the part and thereby distinguish actual defects from intended structural features, such as holes or slots, which also allow magnetic energy radiation from the surface.

Algorithms for performing analytical flaw characterization are known. See Auld, Muennemann & Winslow, *Eddy Current Probe Response To Open And Closed Surface Flaws*, Journal of Nondestructive Evaluation, Vol. 2, No. 1, 1981; Auld, Muennemann, Riziat & Winslow, *Analytical Methods in Eddy Current N.D.E.*, A Review In Progress In Quantitative Nondestructive Evaluation, Vol. 1, 1982, Plenum Press.

An object of the invention is providing eddy current indicia or data for performing analytical characterization of defects.

DISCLOSURE OF INVENTION

According to the invention, a uniform eddy current is impressed in the part, and the field produced by the current is sensed at several directions, and signals are produced for each direction which manifest a characteristic of the current. One signal may represent the phase difference between the excitation current and the field detected from the flaw or defect. Another signal may represent an amplitude or magnitude characteristic of the current.

By producing the signals at different locations along the part, a matrix of data is derived that may then be processed to identify the three-dimensional characteristics of the detected defect. Those characteristics are represented by the complex flow of eddy current relative to the defect.

BEST MODE FOR CARRYING OUT THE INVENTION

Figure 1:
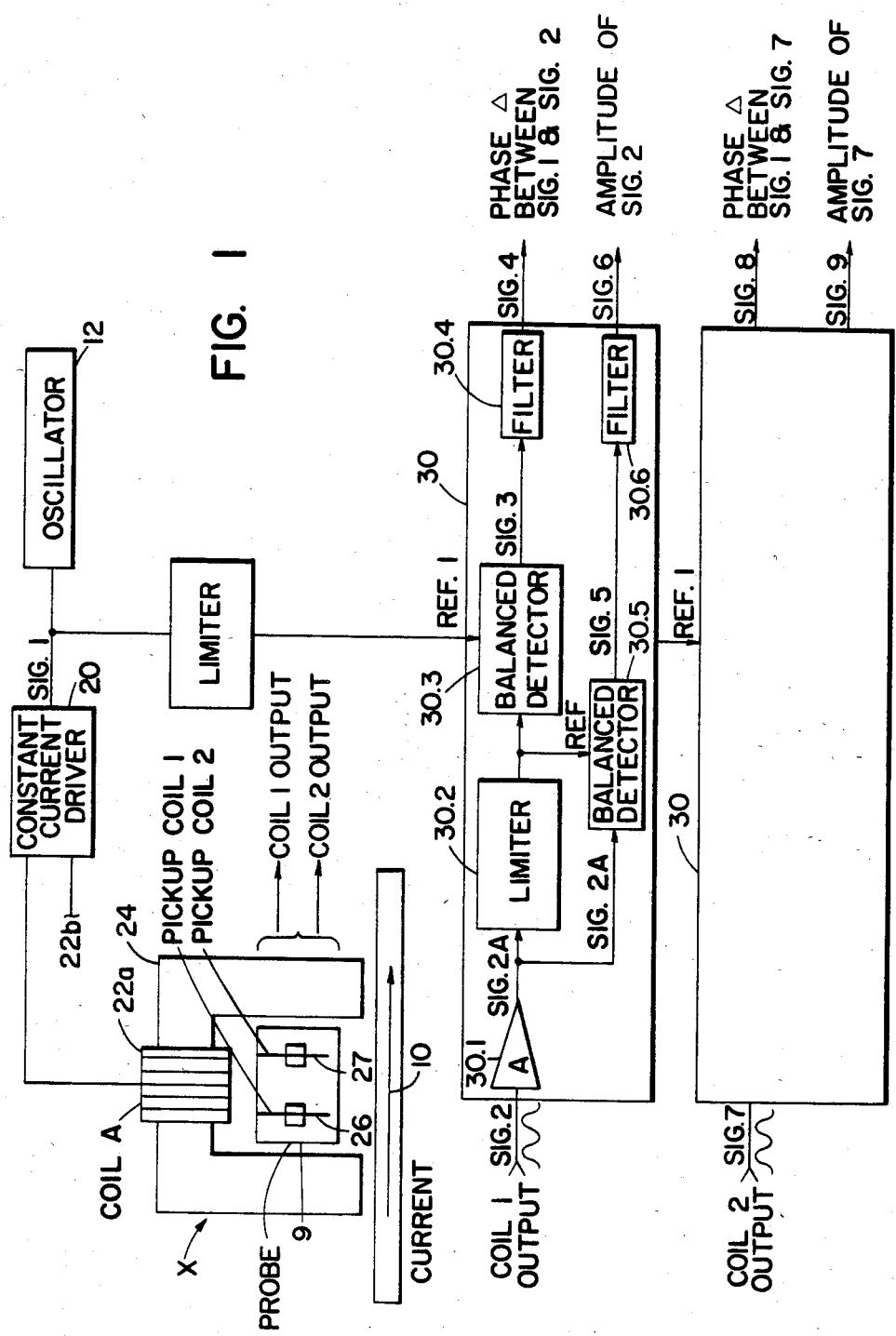
FIG. 1 is a block diagram of an eddy current detection system according to the invention.
Figure 2:
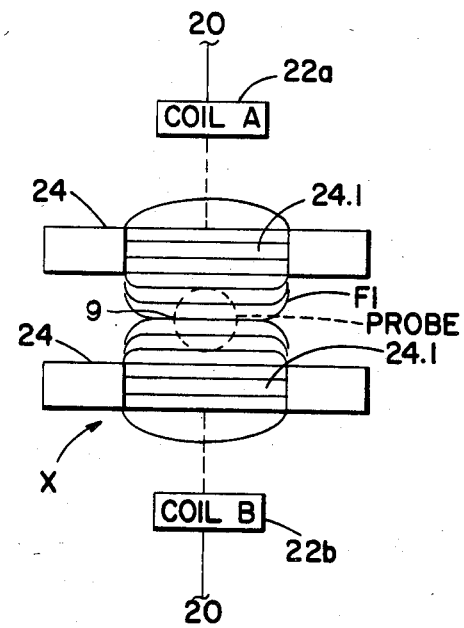
FIG. 2 is an isometric view of a dual coil head device for creating uniform eddy current.

The testing device in FIG. 1 is intended to impress a uniform eddy current in a part 10. To do this, an oscillator 12 provides an alternating signal, SIG 1, to a constant current driver 20 which powers an excitation probe X. FIG. 2 shows that the driver powers two coils, A, B, in the excitation probe X; both are wound in the same direction on a ferrite core 24, with an air gap 24.1. As a result of the overlapping fields, lines F1, between the air gaps, the field between the cores is uniform in density, and this produces (induces) a uniform surface eddy current in a conductive material, such as the part 10. A part of the probe X, a pickup probe 9 (the dotted circle 9) is located in this uniform field area where it senses the eddy current produced EMR (electromagnetic radiation). The pickup probe comprises highly directional electromagnetic coils 1, 2 on cylindrical ferrite cores that are oriented to detect field lines on two orthogonal planes. The pickup probe 9 may be rotated in the X, Y, Z directions (field planes) to detect the field lines at those three positions and produce signals from which the field lines in each direction X, Y or Z may be extrapolated. These coils 1, 2 produce output signals SIG 2, SIG 7, which are processed to yield four signals, SIG 4, SIG 6, from SIG 2 and SIG 8, SIG 9 from SIG 7. SIG 4 represents the phase difference (phase Δ) between the oscillator output SIG 1 and the SIG 2. SIG 6 represents a magnitude characteristic (e.g., absolute amplitude) of the SIG 2. Together, SIG 4 and SIG 6 define a vector element of the current producing them in one orientation of the probe.

Similarly, SIG 8 manifests the phase difference between the coil 2 output SIG 7 and SIG 1 from the oscillator. SIG 9 represents the amplitude of the SIG 7, and again the two define a vector. Thus, for each X, Y or Z position of the coils 1, 2, four signals are produced that manifest the eddy current orientation or direction. By sensing the field at all three positions, twelve signals are developed which function as vector coordinates for the current at a place at which the device X (the coils 24 and the probe 10) is placed.

The four signals SIG 4, 6, 8, 9 are developed in this manner: The SIG 1 signal, at a certain frequency, is supplied to the constant current driver which provides constant power (e.g., constant current) to each coil 22a, 22b. This way there is no change in eddy current magnitude due to reactive interaction (changes in inductive load) between the coils 24A,B and the part. For well-known reasons, the current produces electromagnetic energy that rotates from the surface normal to the direction of the current. The SIG 2 signal that is produced comprises a sinusoidal signal at the same frequency but phase shifted because of reactive effects with the part. Similarly, the coil 2 output signal comprises a sinusoidal signal, SIG 7. Since the two coils are slightly spaced apart, the signals SIG 2 and SIG 7 do represent the field characteristics at two somewhat different points with respect to the part's 10 surface. Thus, slight differences between the two coil outputs will reveal changes in current direction, hence, characteristics of the article, specifically those in the surface region. The SIG 2 and SIG 7 signals are each processed in a processing unit 30. The SIG 2 signal is supplied to an amplifier 30.1 that produces an output signal SIG 2A. The signal 2A is supplied to a limiter 30.2, whose purpose is to maintain a constant amplitude SIG 2A at its output. That output is applied to a balanced phase detector, which receives a reference signal, REF 1, from a limiter 30.2. The input to this limiter is the SIG 1 and the output from the limiter is the REF 1 which is maintained, by the limiter, at a constant amplitude. The output from the balanced phase detector is a signal SIG 3 which represents the phase difference, if any, between the SIG 2A and REF 1. SIG 3 is supplied to a low pass filter to produce a signal, SIG 4, which represents the absolute phase difference between the SIG 1 and SIG 2. The same process occurs with respect to the coil 2 output (SIG 7) for producing SIG 8.

SIG 2A (from the amplifier 30.1) is also supplied to another balanced phase detector 30.5, whose reference signal is the output from the limiter 30.2. SIG 2A has the same phase characteristics as the coil 1 output, SIG 2. The balanced phase detector 30.5 produces SIG 5 on its output, and this signal's magnitude is proportional to the relative amplitude of the signal SIG 2A. This happens because the phase of the reference REF and the input, SIG 2A, is the same. SIG 5 is supplied to a low pass filter 30.6, which produces SIG 6, and it represents the absolute amplitude of SIG 2. Again, the same process occurs in the unit 30 associated with the coil 2 output. That is, in that unit 30, the SIG 7 is processed in the same manner as SIG 2 for the coil 1 output to produce SIG 7 which manifests the absolute amplitude of SIG 7.

This apparatus may be used in a number of different ways in order to provide a matrix of data comprising the SIG 4, SIG 6, SIG 8 and SIG 7 produced by the coil 1 and coil 2. This may be done by moving the whole assembly X along the surface of the article and recording the resultant changes in those signals with the probe in each position X, Y, Z plane.

Obviously, just one coil may be used (although two is preferred, to generate just one pair of phase and amplitude signals (e.g., SIG 4, SIG 6). In addition, one detector 30 may be used with two coils by rapidly switching (commutating) it between the coil outputs.

The foregoing is a description of the preferred embodiment of the present invention. In addition to any modifications and variations that have been described or suggested in the foregoing, others may be made by one skilled in the art without departing from the true scope and spirit of the invention.

We claim:

1. Apparatus for providing indicia of the surface region characteristics of an electrically conductive article, comprising:
    two electromagnetic field generating heads in close proximity for creating an area of uniform field in the article under test;
    oscillator means for providing a constant current alternating drive signal to the heads for energization thereof;
    said apparatus characterized by:
    probe means positioned between said heads within the uniform field for providing for each of three orthogonal directions, two probe output signals from the field produced by eddy current in the article exposed to the uniform field, each of said probe output signals manifesting the field strength of the eddy current-produced field in two orthogonal directions at one of two adjacent positions in the third direction;
    first detection means for providing a first signal that represents the magnitude of the phase difference between each prove output signal and the drive signal;
    second detection means for providing a second signal that manifests a characteristic of the magnitude of each output signal:
    said probe means comprising a field pickup coil for providing each probe output signal.

2. Apparatus according to claim 1, further characterized by:
    separate means associated with each probe output signal for providing said first and second signals, said means comprising said first and second detection means.

3. A method for providing indicia of the surface region characteristics of an electrically conductive article, comprising:
    placing two electromagnetic field generating heads in close proximity for creating an area of uniform field in the article under test;
    providing a constant current alternating drive signal to the heads for energization thereof;
    said method characterized by:
    providing for each of three orthogonal directions two output signals from the field produced by eddy current in the article exposed to the uniform field, each of said probe output signals manifesting the field strength of the eddy current-produced field in two orthogonal directions at one of two adjacent positions in the third direction;
    providing a first signal that represents the magnitude of the phase difference between each probe output signal and the drive;
    second detection means for providing a second signal that manifests a characteristic of the magnitude of each probe output signal.

* * * * *

UNITED STATES PATENT AND TRADEMARK OFFICE
CERTIFICATE OF CORRECTION

PATENT NO. : 4,594,549

DATED : June 10, 1986

INVENTOR(S) : Eugene Smith, et al

It is certified that error appears in the above-identified patent and that said Letters Patent is hereby corrected as shown below:

Column 3, line 19, "coils 24A,B" should read --coils 22a,22b--.

Column 4, line 35, "prove" should read --probe--.

Signed and Sealed this

Twenty-first Day of October, 1986

[SEAL]

Attest:

DONALD J. QUIGG

Attesting Officer

Commissioner of Patents and Trademarks